United States Patent
Thomas et al.

(10) Patent No.: US 6,763,696 B1
(45) Date of Patent: Jul. 20, 2004

(54) SHOCK TUBE

(75) Inventors: James Kelly Thomas, San Antonio, TX (US); Michael J. Lowák, San Antonio, TX (US); Adrian J. Pierorazio, San Antonio, TX (US); Quentin A. Baker, San Antonio, TX (US); Ming Jun Tang, Andover, MA (US); James W. Wesevich, San Antonio, TX (US); Michael A. Polcyn, San Antonio, TX (US)

(73) Assignee: Baker Engineering and Risk Consultants, Inc., San Antonio, TX (US)

( * ) Notice: Subject to any disclaimer, the term of this patent is extended or adjusted under 35 U.S.C. 154(b) by 0 days.

(21) Appl. No.: 10/046,911

(22) Filed: Jan. 17, 2002

Related U.S. Application Data

(60) Provisional application No. 60/261,823, filed on Jan. 17, 2001.

(51) Int. Cl.[7] .................................................. G01M 7/00
(52) U.S. Cl. ..................................................... 73/12.09
(58) Field of Search ........................... 73/12.01, 12.08, 73/12.09, 11.04, 147, 865.6

(56) References Cited

U.S. PATENT DOCUMENTS

| | | | |
|---|---|---|---|
| 3,652,434 A | * 3/1972 | Bar-Nun et al. | 204/157.82 |
| 3,729,980 A | * 5/1973 | Johnson et al. | 73/12.08 |
| 3,776,578 A | * 12/1973 | Jessup et al. | 28/94 |
| H000086 H | * 7/1986 | Kingery et al. | 73/12.08 |
| 5,181,418 A | * 1/1993 | Bartscher et al. | 73/146.3 |
| 5,197,323 A | * 3/1993 | Osofsky | 73/12.01 |
| 5,366,013 A | * 11/1994 | Edwards et al. | 166/297 |
| 5,396,966 A | * 3/1995 | Roos et al. | 175/45 |
| 5,405,779 A | * 4/1995 | McCabe et al. | 435/285.3 |
| 5,511,714 A | * 4/1996 | Bauer et al. | 227/130 |
| 5,598,904 A | * 2/1997 | Spyche, Jr. | 188/287 |
| 5,606,110 A | * 2/1997 | Lacey, Jr. | 73/12.08 |
| 5,996,570 A | * 12/1999 | Legate | 73/12.08 |
| 6,164,810 A | * 12/2000 | Derezinski | 366/75 |
| 6,592,545 B1 | * 7/2003 | Bellhouse et al. | 604/69 |

* cited by examiner

*Primary Examiner*—Max Noori
(74) *Attorney, Agent, or Firm*—McDermott Will & Emery LLP

(57) ABSTRACT

A shock tube comprises a driver section, an expansion section connected to the driver section, and an extension connected to the expansion section. Shock absorbent material is disposed within a cavity defined by the driver section and extension section. At least one active vent is disposed over respective holes in the extension section that are connected to the cavity. The extension section is adjustable between one of at least two positions such that a length of the extension section in a first position is longer than a length of the extension section in a second position. The length of the gas column contained within the driver section can also be adjusted by the position of a movable bulkhead.

20 Claims, 17 Drawing Sheets

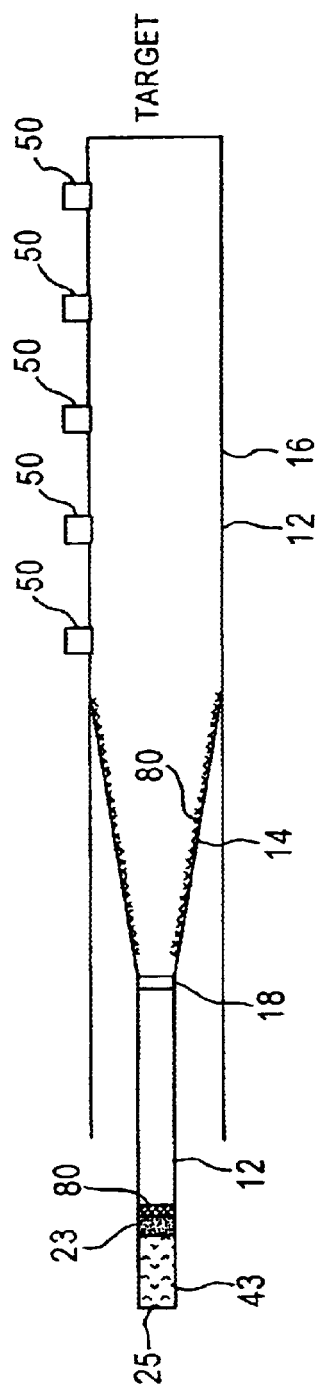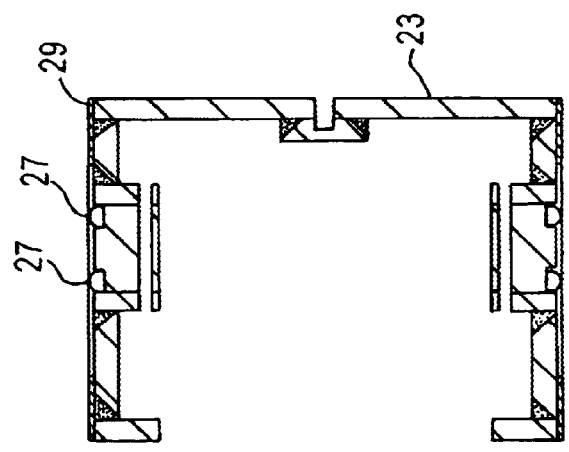

FIG. 3
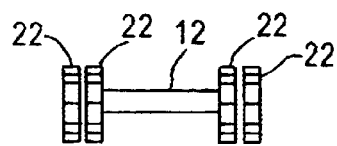 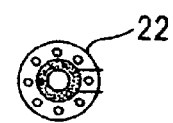
FIG. 4a  FIG. 4b
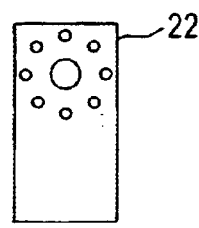 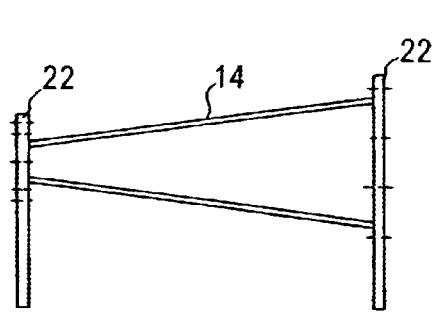 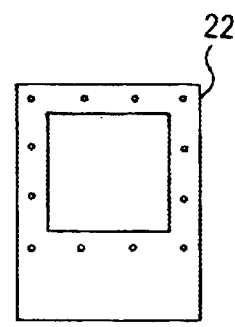
FIG. 5a  FIG. 5b  FIG. 5c
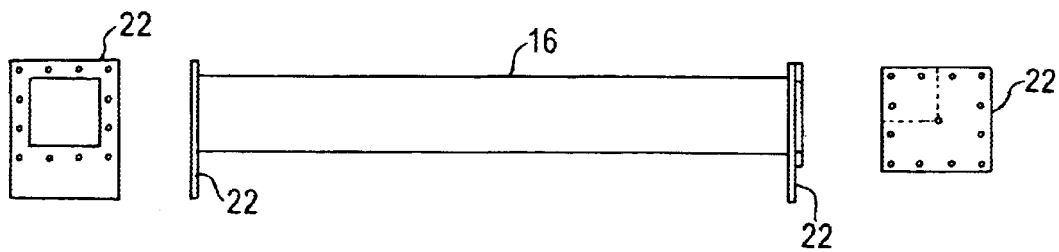
FIG. 6a  FIG. 6b  FIG. 6c

SHOCK TUBE

CROSS REFERENCE TO RELATED APPLICATIONS

This application claims the benefit of U.S. Provisional Application No. 60/261,823, filed on Jan. 17, 2001, incorporated herein by reference.

FIELD OF THE INVENTION

The invention relates generally to testing equipment and, more specifically, to an improved shock tube.

BACKGROUND OF THE INVENTION

A shock tube can be employed for determining the effects of a shock wave on a test or target object. The shock wave is generated by the sudden release of high-pressure gas from within the shock tube driver section. This shock wave provides the primary loading on the target. As the shock wave expands out of the discharge end of the driver, a rarefaction wave is generated which travels into and along the driver. The reflections of the initial shock wave off the target and of the rarefaction off the closed end of the driver may interact to yield secondary loading on the target. Depending on the shock tube geometry, the rarefaction wave can yield a period of reduced or negative pressure on the target.

Very large cylindrical shock tubes can be used when the test or target object is large. However, large shock tubes are very expensive to manufacture, install, and operate. Shock tubes utilizing reduced driver diameters with an expansion section to obtain the desired target dimensions have been therefore employed to minimize these costs.

In an ideal free-field simulation, the pressure loading on the test object rises abruptly to a maximum positive value, decays smoothly at a predetermined rate to a zero pressure value, goes negative, and then rises smoothly at a predetermined rate back to a zero pressure. However, the presence of the expansion section increases the magnitude and effect of rarefaction waves on the test object, and can terminate the primary target positive phase loading prematurely. The secondary waves generated by the interactions of the reflected primary shock and the rarefaction wave can also prevent this idealized target loading from being achieved.

The duration and impulse of the pressure waves generated by a shock tube are governed partially by the length of the driver and extension sections. The use of fixed-length driver and extension sections severely limits the range of achievable target load histories. The use of multiple driver and extension sections can overcome this restriction, but this increases the manufacture, installation, and operation costs. In addition, the target load histories that can be achieved are still limited by the available driver and extension section lengths.

There is, therefore, a need for an improved shock tube that allows the rarefaction and secondary shock waves to be controlled such that the idealized target loading can be more closely approximated, and that allows the duration and impulse of the pressure waves to be controlled without the need for multiple driver and extension sections.

SUMMARY OF THE INVENTION

These and other needs are met by the present invention, which in accord with one aspect includes a driver section, an expansion section connected to the driver section, an extension section joined to the expansion section, and shock absorbent material. The driver and expansion sections define a cavity and the shock absorbent material is disposed within this cavity. The shock absorbent material can be disposed on the expansion section sidewalls and proximate to the driver section end wall. By placing shock absorbent material at the end of the driver section, the reflection of the initial rarefaction wave and subsequent shock and rarefaction waves can be mitigated from this surface. Also, shock absorbent material placed in the expansion section can mitigate shock wave reflections from the section sidewalls.

In another embodiment of the present invention, the shock tube includes a driver section, an expansion section connected to the driver section, an extension section joined to the expansion section, and one or more active vents disposed over respective holes in the expansion and/or extension sections connected to the cavity defined by these sections. The shock tube can include two or more active vents that are separate from one another or are connected together with a common manifold. The active vents are employed to control the shape of both the positive and negative target loading phases.

In yet another embodiment of the present invention, the shock tube includes a driver section, an expansion section connected to the driver section, and an extension section joined to the expansion section. The length of the gas space within the driver section is adjustable, so that a wide range of effective driver lengths can be achieved. This facilitates control of the shape of both the positive and negative target loading phases.

In still another embodiment, the shock tube includes a driver section, an expansion section connected to the driver section, and an extension section joined to the expansion section. The extension section length is adjustable, so that a wide range of effective extension section lengths can be achieved. This facilitates control of the shape of both the positive and negative target loading phases.

Additional advantages of the present invention will become readily apparent to those skilled in this art from the following detailed description, wherein only an exemplary embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein:

FIG. 1b is a cross-sectional side view of a shock tube;

FIG. 2a is a cross-sectional, partial view of the shock tube shown in FIG. 1a;

FIG. 2b is a cross-sectional, partial view of a movable bulkhead shown in FIG. 1b;

FIG. 3 is a side view of a driver section;

FIG. 4a is an exploded side view of a driver section and flanges;

FIG. 4b is a rear view of the flange shown in FIG. 4a;

FIG. 5a is a rear view of an expansion section;

FIG. 5b is a side view of an expansion section;

FIG. 5c is a front view of an expansion section;

FIG. 6a is a front view of an extension section;

FIG. 6b is a side view of an extension section;

FIG. 6c is a front view of an extension section;

DETAILED DESCRIPTION OF THE PREFERRED EMBODIMENTS

Figure 1A:
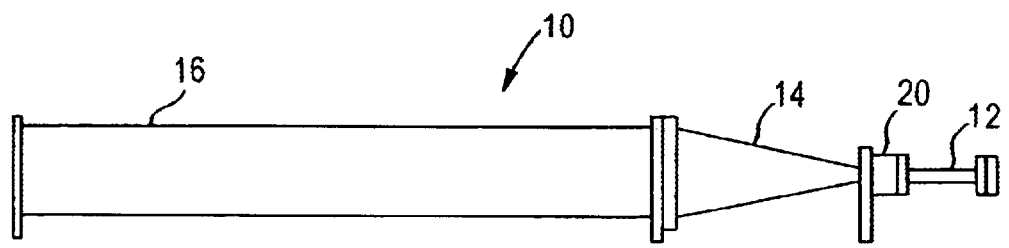
FIG. 1a is a schematic side view of a first embodiment of a shock tube in accord with one aspect of the invention.
Figure 2A:
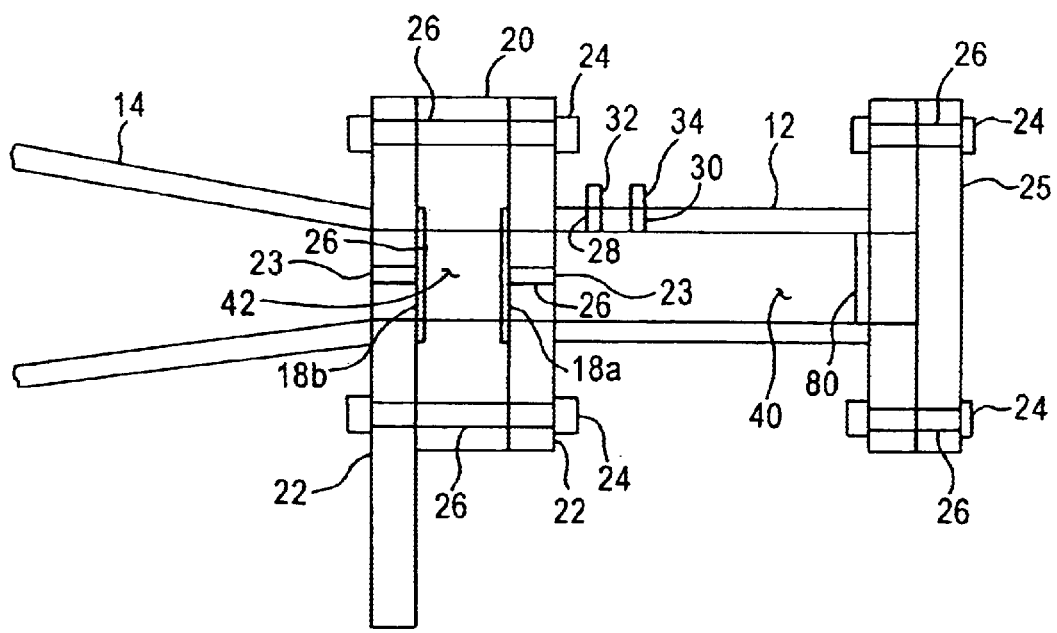

A shock tube in accordance with an aspect of the invention, is illustrated in FIGS. 1–6. The shock tube 10 includes a driver section 12, expansion section 14, and an extension section 16. Although shown as separate sections, the expansion section 14 and the extension section 16 can be formed as a single section. The expansion section 14 can act as a transition from the cylindrically-shaped driver section 12 to the square-shaped extension section 16, although neither the driver section 12 nor the extension section 16 is limited as to a particular cross-sectional shape.

During use, one or more diaphragms 18 are located between the driver section 12 and the expansion section 14. When two diaphragms 18a, 18b are used, for example, a spool section 20 can be provided. The sections 12, 14, 16, 20 of the shock tube can also each include flanges 22 located at each end of the section. The flanges 22 can be used to connect the sections 12, 14, 16, 20 to one another using connectors, such as bolts 24 that pass through bolt holes 26 in the flanges 22. The connectors can be removable, and in so doing, the sections 12, 14, 16, 20 can be removable from one another. In this manner, for example, driver sections 16 and/or extension sections 16 with different lengths can be swapped, which allows for a shock tube 10 with a greater flexibility.

The flanges 22 can also be used to hold the diaphragms 18a, 18b, and each flange 22 that holds the diaphragms 18a, 18b can include a recess 26 about a center hole 23 in the flange 22 to aid in gripping the diaphragms 18a, 18b. A rear wall 25 can also be used to seal one end of the driver section 12. In a dual diaphragm system, two separate gas spaces 40, 42 are provided within the shock tube 10. The first gas space 40 is located in the driver section 12, and the second gas space 42, typically much smaller than the first gas space 40, is located between the two diaphragms 18a, 18b. During fill operations, the pressure in the second gas space 42 between the two diaphragms 18a, 18b is maintained at approximately half of the pressure in the first gas spacer 40 located in the driver section 12. The pressure load across either diaphragm 18a, 18b is, therefore, about half what the pressure would be if only a single diaphragm was used. Thus, a driver pressure equal to slightly less than twice the diaphragm pressure capacity can be achieved.

In operation, venting the second gas space 42 between the diaphragms 18a, 18b causes the pressure across the first diaphragm 18a to increase until the first diaphragm 18a ruptures. The rupturing of the first diaphragm 18a subsequently causes the second diaphragm 18b to rupture and release a shock wave into the expansion section 14. In addition to increasing the driver pressure that can be achieved with a given diaphragm material, the use of a dual diaphragm system allows the shock strength to be closely controlled over a continuous pressure range so that highly repeatable results can be achieved.

The driver section 12 and, if used, the spool section 20 can include one or more connections 28, 30 through the driver and spool sections 12, 20. These connections 28, 30 can be used, for example, to provide access for a pressure measurement device or transducer 32 and a filling and/or venting line 34. The pressure transducer 32 measures the pressure within the driver or spool section 20, and the filling/venting line 34 is used to supply fluid/gas to and/or exhaust fluid/gas from the driver or spool section 20. Additional connections 36 for pressure transducers 38 can also be provided on the expansion and extension sections 14, 16.

Figure 7A:
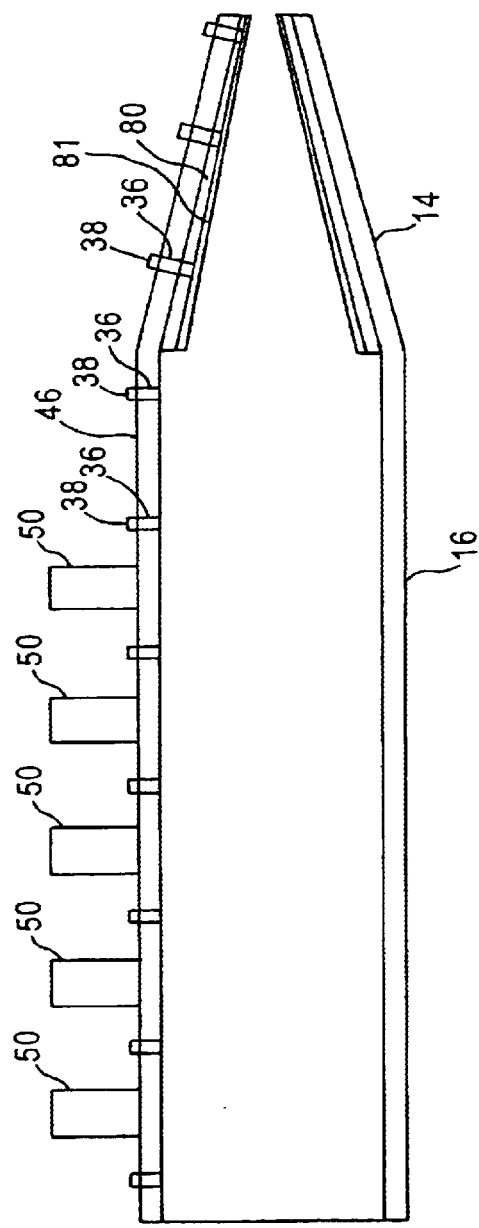
FIG. 7a is a cross-sectional, partial view of a shock tube with active vents.

Although not limited in this manner, ten pressure transducers 38 are positioned at ten stations along the length of the expansion and extension sections 14, 16, as illustrated in FIG. 7a. Of the ten transducers 38; three are positioned in the expansion section 14. A non-limiting example of a pressure transducer 38 is a PCB Model 102A flush-mounted quartz units, manufactured by PCB of Depew, N.Y. To partially shield the transducers 38 from shock tube vibration, the transducers 38 are fitted into plastic transducer mounts 36 that were separated from the shock tube wall 46 by a rubber gasket. The signals from the pressure transducer 38 can be conditioned using a PCB Model 483B07 conditioning power unit. A digitizing system, such as a LeCroy 6810 manufactured by LeCroy of Depew, N.Y., converts the data to digital form. The digitizer is triggered via an amplified signal from the pressure transducer 38 closest to the driver section 12. Although not limited in this manner, the pressure data was sampled at a rate of one reading per microsecond over a period of 131 msec.

As illustrated in FIGS. 1a and 1b, the shock tube 10 can include a driver section 12 having a variable fluid/gas capacity. Although any driver section 12 capable of having a variable capacity is acceptable for use with the shock tube 10, in a current aspect, the driver section 12 includes a movable bulkhead 23. The bulkhead 23 defines another space 43 between the bulkhead 23 and the rear wall 25. Alternatively, the bulkhead 23 can act as a movable rear wall. Although not limited in this manner, in operation, fluid can be introduced into the third space 43 through connections (not shown) and pressurized or depressurized to move the bulkhead 23 towards or away from the target. In so doing, the capacity of the driver section 12 can be varied. By providing a driver section 12 with an adjustable capacity, a single shock tube 10 can produce a wider range of positive and negative phase target pressure loadings.

The bulkhead 23 can includes seals that prevent fluid in the third space 43 from entering into the second gas space 42 or alternatively prevent gas/fluid in the second gas space 42 from entering the third space 43. The bulkhead 23 can also include slides that allow for smooth sliding of the bulkhead 23 within the driver section 12.

The shock tube 10 can also include one or more active vents 50 located on the extension section 16. The vents 50 can advantageously limit both end-wall loading and shock reverberations within the shock tube 10. As used herein, an active vent 50 is a vent with a cover system that opens at the initiation of a positive pressure phase and closes near the end of the positive pressure phase or the beginning of the negative pressure phase.

Figure 8:
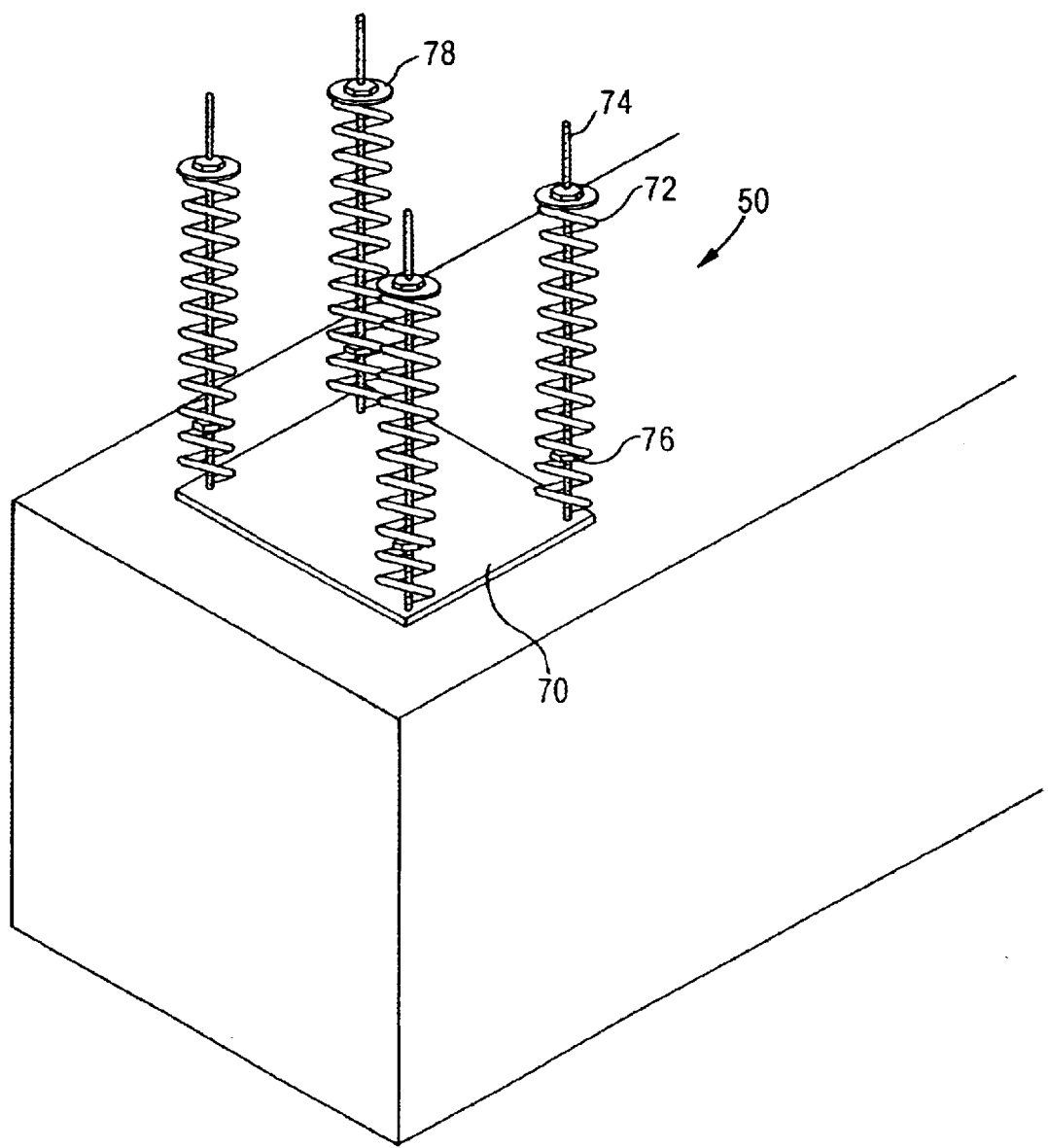
FIG. 8 is an example of an active vent.

An example of an active vent 50 is illustrated in FIG. 8. The active vent 50 includes a vent cover 70 and four springs 72, which each spring 72 at a corner of the vent cover plate 70. The springs 72 can be supported on and guided by threaded rods 74. A nut threaded onto the rod 74 inside the spring 72 can serve as an adjustable plate travel stop 76. A threaded nut and washer pre-load assembly 78 placed onto the rod 74 above the spring 72 allows the force resisting plate motion to be varied.

Figure 9:
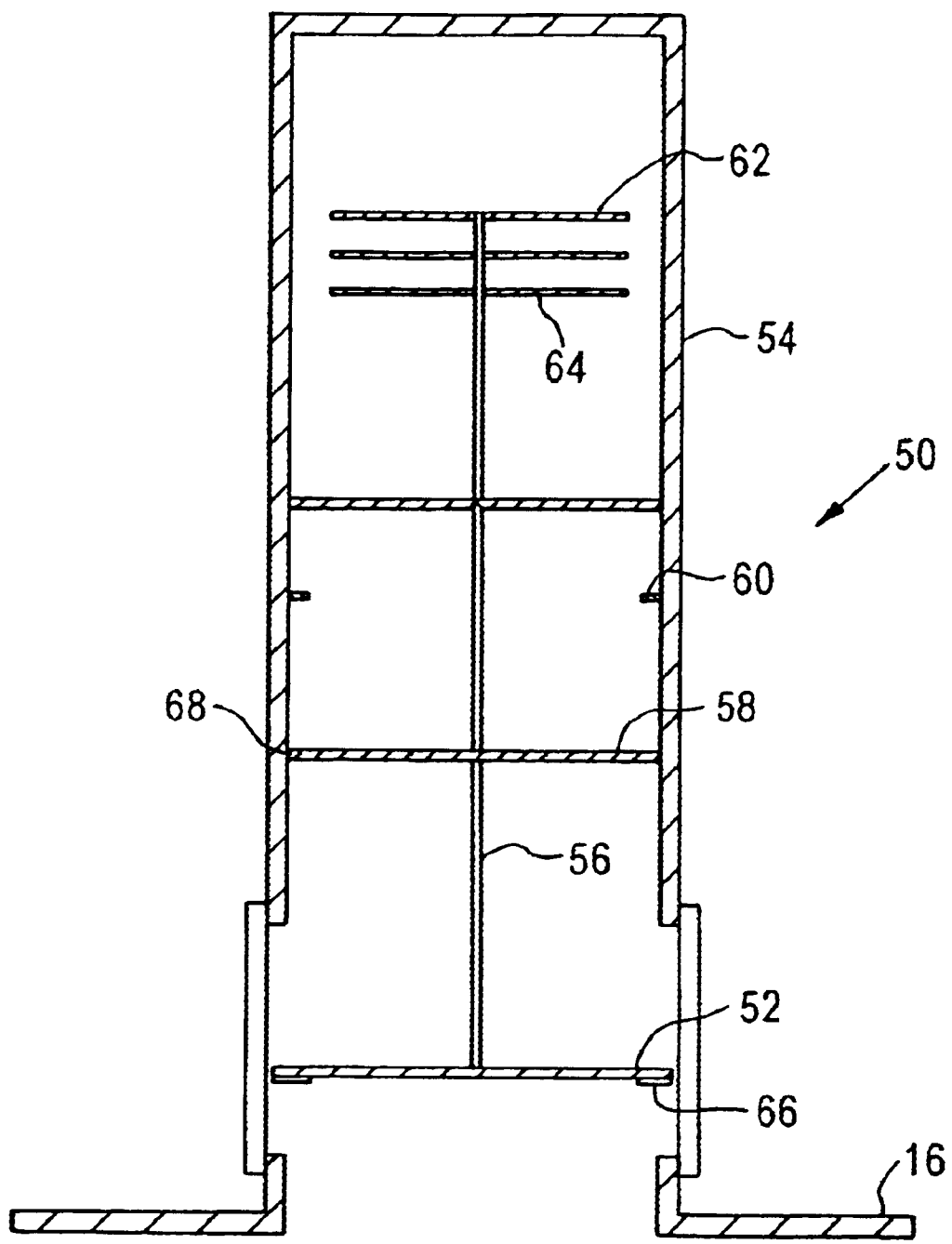
FIG. 9 is another example of an active vent.

Another example of an active vent 50 is illustrated in FIG. 9. The active vent 50 is a piston 54 that includes a vent seal plate 52 that rests on and seals off the extension section 16 prior to the arrival of the shock. The positive pressure developed under the vent seal plate 52 due to the passage of the shock forces up the vent seal plate 52 and compresses the gas in the piston 54. Subsequently, as the pressure in the extension section 16 decreases, the pressure in the gas piston 54 forces the vent seal plate 52 back down onto the extension section 16. Thus, the vent 50 opens on positive pressure and closes as the negative phase arrives.

A shaft 56 can connect the vent seal plate 52 to an upper piston head 58. The vent can also include an upper stop 60 that prevents the upper piston head 58 from traveling too far up into the piston 54. If the head 58 is not stopped, under some conditions, the pressure in the piston 50 could be excessive, and the resulting downward velocity of the vent seal plate 52 can be very large. The upper stop 60 can be, for example, a welded ring or a thicker wall section created by milling the inner diameter of a lower section.

Figure 10:
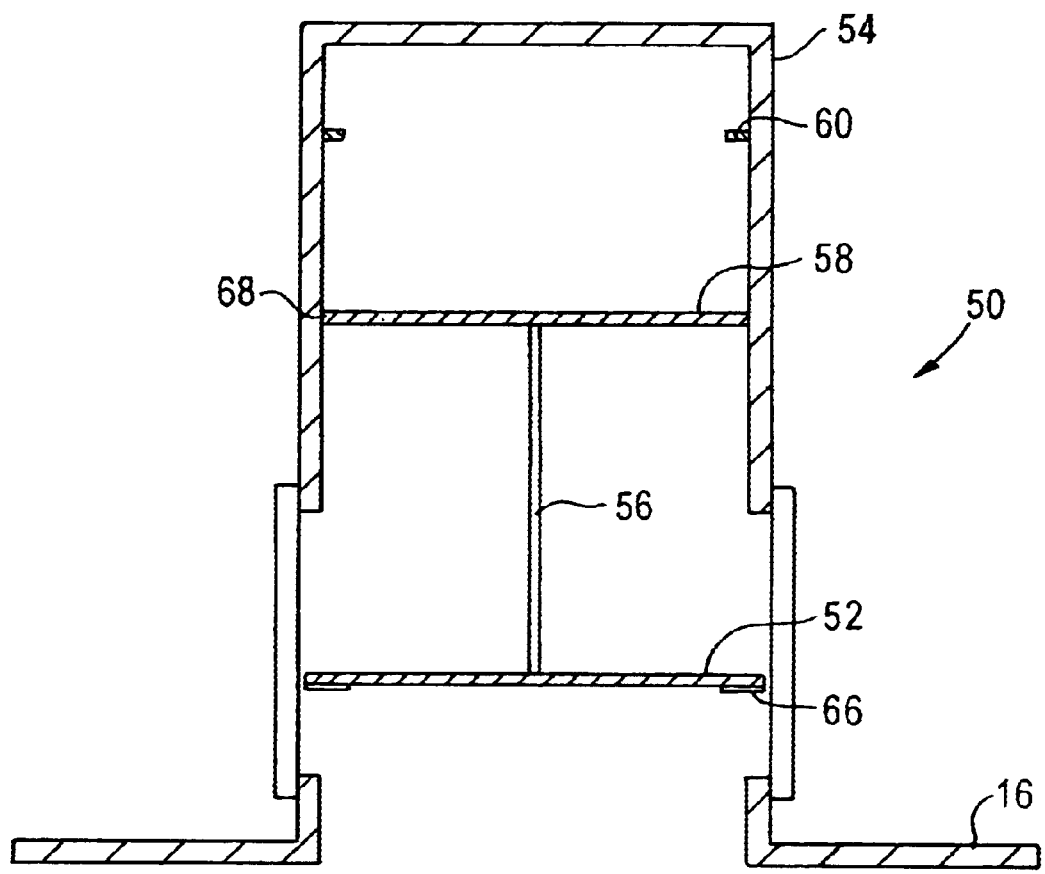
FIG. 10 is still another example of an active vent.

The active vent 50 can also include a dashpot 62, which is used to limit the maximum velocity of the piston head 58, since the drag force exerted by the dashpot elements 64 would be proportional to the square of the head velocity. A dashpot 62 could be used, for example, if the velocities of the head 58 would result in damage to the seal plate 52 or extension section 16. An example of an active vent 50 without a dashpot is illustrated in FIG. 10. Although not shown, a dead stop spring assembly can be placed at the top of the assembly, and an inert gas mixture (e.g., nitrogen) can be employed in the gas piston 54.

The use of an active vent system provides a significant degree of operational flexibility. The response of the vent 50 to a specified shock pressure history is determined by the diameter and height of the piston gas region, the vent diameter, the combined mass of the seal plate 52 and piston head 58, the location of the stop 60, the configuration of the dashpot 62, and the initial pressure of the gas inside the piston 54. While all of the parameters except the initial piston gas pressure can be fixed, this single parameter allows the response of the vent 50 to be adjusted over a fairly wide range.

The gas pressure, for example, can be increased to a level that the vent 50 would not open. A small initial piston gas pressure would provide some resistance, such that opening of the vent 50 would be delayed until the shock was well past the vent 50. This can be beneficial in limiting the impact of the resulting rarefaction wave on the shock. A small initial pressure also increases the pressure developed in the piston 54 and, hence, the speed at which the vent closes. Leaving the piston gas at atmospheric pressure reduces the vent resistance and, hence, maximizes the impact of the vent 50 on the positive phase. Furthermore, a vacuum can be pulled on the piston 54 to partially counteract the combined mass of the seal plate 52 and piston head 58 to facilitate vent opening with very low shock pressures.

Figure 7B:
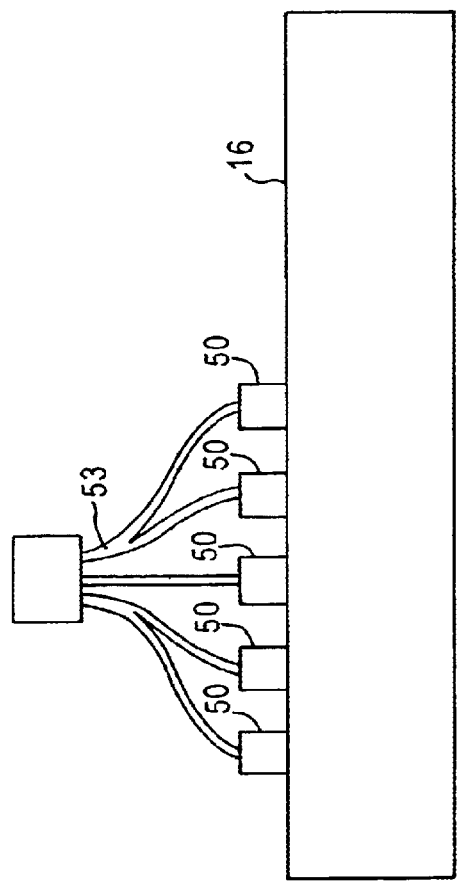
FIG. 7b is a partial view of a shock tube with ganged active vents.

The vent 50 can also includes seals 66, 68 respectively between the piston 54 and the seal plate 52 and between the piston 54 and the piston head 58. However, the seals 66, 68 do not necessarily have to be leak-tight, as the entire vent operation cycle would be less than one second in duration. In one aspect of the invention, the seal 66, 68 is capable of allowing the initial gas piston pressure to be set accurately A distribution of active vents 50 on the extension section 16 can be operated as separate units such that the gas piston pressure for each vent 50 can be set individually (illustrated in FIG. 7a), or the vents 50 can be operated with groups of vents 50 ganged together on a common gas manifold 53 (illustrated in FIG. 7b). A ganged arrangement can offer advantages in terms of operational simplicity. Additionally, a latching mechanism (not shown) can be included to allow a vent cover to lift off the vent 50 but not reseat. Thus, actuating the latching mechanism would allow an active vent 50 to operate as an open-only vent.

Figure 11:
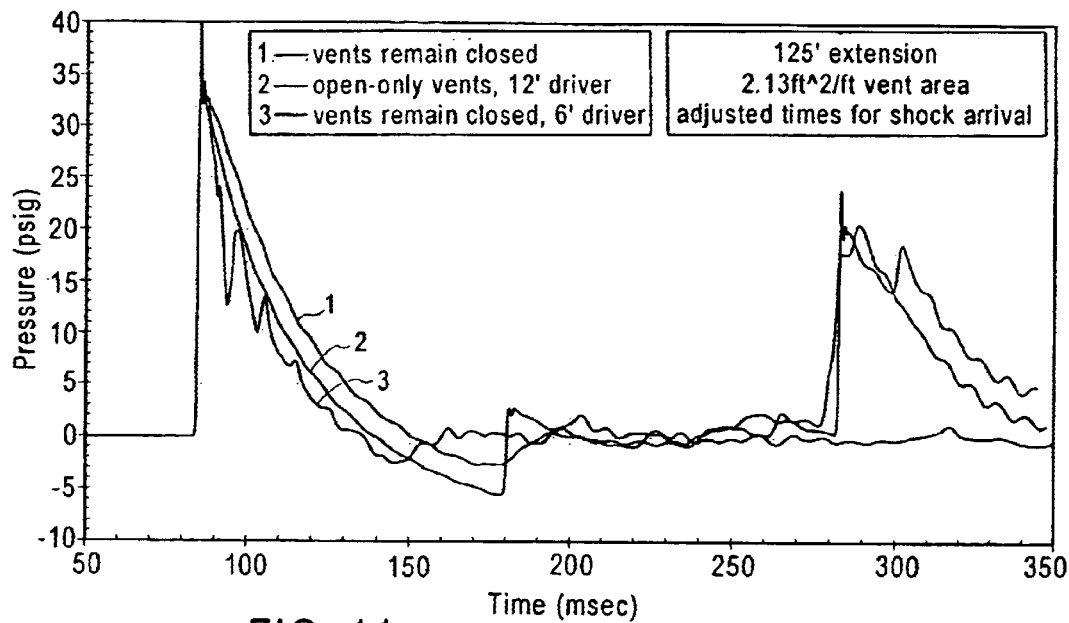
FIG. 11 is a graph of the effect of open-only vents.

FIG. 11 illustrates calculated target pressure histories for the base case with no vents, with open-only vents, and with a driver gas column length half that of the base case (i.e., 6 feet long) with no vents. The shock arrival times for the pressure histories shown in the figures have been adjusted so that they are equal in order to simplify comparisons between different configurations. The negative phase for the base case with no vents terminates after about 40 msec due to the arrival of a pressure wave originating in the expansion section. This pressure wave arrives at approximately 180 msec and is formed by a combination of the collapse of the vacuum developed in the expansion section and counter shock waves reflected off the closed end of the driver.

The shock wave that arrives at approximately 280 msec is formed by the passage of the main shock back down into the expansion section, and is due to a partial reflection of this shock back towards the target. The secondary shock arriving at 300 msec is the reflection of the main shock wave off the closed end of the driver. Utilizing open-only vents significantly decreases the duration and impulse associated with the positive phase by allowing gas behind the shock wave to escape the tube and by allowing a series of rarefaction waves to enter the tube. The vents also allow gas to flow into the tube during the negative phase, so that the duration of the negative phase is also decreased. The negative phase duration is cut in half for this case by the use of open-only vents.

The vents can prevent substantially all of the secondary waves discussed above from reaching the target. The impact of a vent on these secondary waves is more pronounced than on the initial shock, since the vent is already open when a secondary wave passes by, some of these waves are created by the reflected shock (which the vents weaken), and the reflected shock must pass by the same vent twice. Most of the pressure oscillations during the initial positive phase shown in FIG. 11 for the case with vents are an artifact of the numerical model used to calculate the graphs. Representing the vent opening as a small number of four discrete steps rather than as a smooth and continuous event introduces a series of flow and pressure field perturbations in the vicinity of the vent that subsequently propagate down the shock tube and impact the target.

The example shown in FIG. 11 with the driver length cut in half compares the positive phase impulse reduction obtained with a shortened driver to that produced by venting. The impulse reduction due to venting is larger for this case than that obtained by cutting the driver length in half. The negative phase amplitude is approximately twice that with the longer driver. The termination of the negative phase with the shorter driver is due to the arrival of the counter shock reflection off the closed end of the driver, and is much more pronounced than with the longer driver. The pressure wave from the expansion section and reflection of the main shock off the closed end of the driver arrive at essentially the same time (280 msec) in this case.

Figure 12:
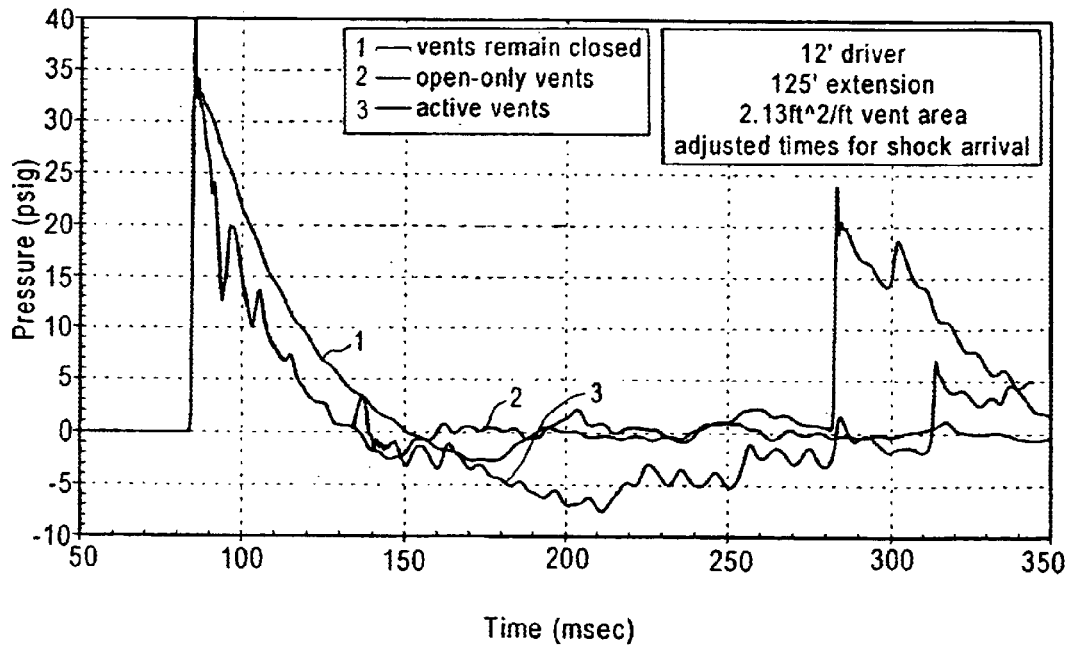
FIG. 12 is a graph of the effect of active vents.

FIG. 12 illustrates target pressure histories for the base case with no vents, with open-only vents, and active vents. The first two of these pressure histories were shown in FIG. 11 The pressure histories with the open-only and active vents are identical until near the end of the initial positive phase. However, the closure of the active vents allows a significant negative phase to develop. The duration of the negative phase achieved with the active vents is over four times as long as that with no vents, and over seven times as long as that with open-only vents. Furthermore, the negative pressure developed with the active vents is three times as great as with no vents or open-only vents. The negative phase impulse achieved with active vents is nine times larger than that with no vents, and seventeen times larger than that with open-only vents.

The pressure histories shown in FIG. 12 illustrate the negative phase enhancements that can be achieved via the use of active vents. The magnitude of the secondary shock and pressure waves arriving at the target are also significantly decreased by the use of active vents, although the reduction is not as great as with the equivalent area of open-only vents. As noted previously, the reduction in the amplitude of these secondary waves would actually be greater with active vents than shown here since only one cycle of active vent operation was included in the numerical model.

Figure 13:
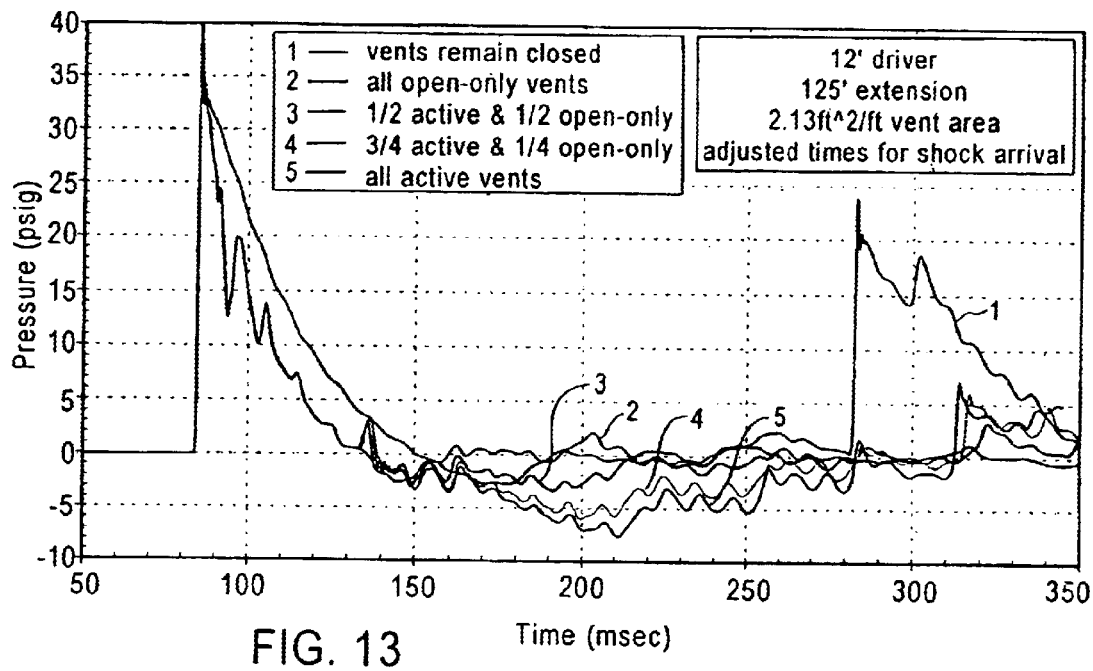
FIG. 13 is a graph of the effect of mixture of open-only and active vents.

FIG. 13 illustrates the same target pressure histories provided in FIG. 12 and also shows the histories for 50% of the vents being active and for 75% of the vents being active. The same total vent area is present in all cases. This figure illustrates the effect of utilizing a blend of active and open-only vents. The target pressure history can be tailored between these limits by altering the mixture of open-only and active vents.

Although not illustrated by this figure, the position and fraction of vents that are active play a role in defining the target pressure history. The vents near the beginning of the extension section (i.e., near the expansion section) have the largest impact on the duration and intensity of the negative phase, while those near the extension section end (i.e., near the target) exert the most influence on the loading of the target by secondary pressure and shock waves. Hence, by varying the mixture of open-only and active vents along the extension section, the target pressure history can be controlled to an even greater degree than indicated by FIG. 13.

Figure 14:
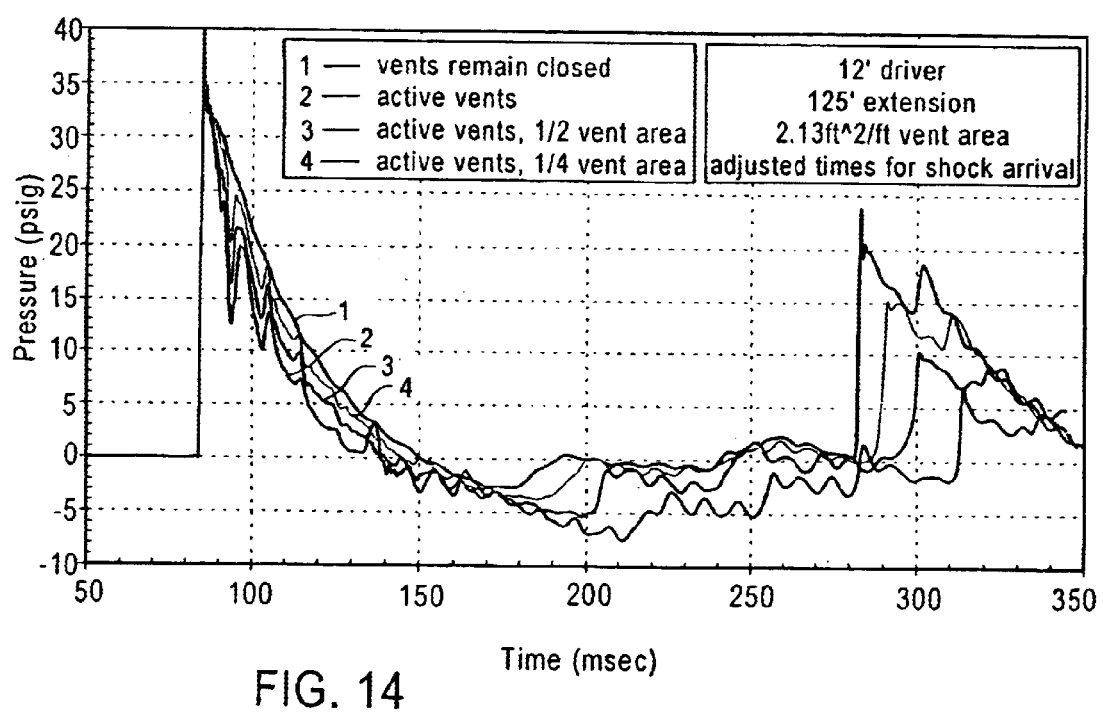
FIG. 14 is a graph of the effect of active vent area.

FIG. 14 illustrates target pressure histories for the base case with no vents, with active vents, with active vents but with only half of the nominal vent area, and with active vents but with only one-quarter of the nominal vent area. This figure illustrates the effect of reduced vent area. As can be seen, the impact of the vents on the target pressure history transitions smoothly with the amount of vent area provided.

The results discussed above demonstrate that venting the shock tube decreases the positive phase impulse and duration and limits the intensity of secondary pressure and shock waves; open-only vents limit the duration of the negative phase; active vents increase the both duration and amplitude of the negative phase; and the negative phase parameters can be controlled by the total vent area made available along with the mixture and distribution of active and open-only vents employed.

A long extension section 16 is typically used to achieve a long duration negative phase. That is, an extended time period between the arrival of the main shock wave and subsequent waves is required in order to develop an extended negative phase, since the arrival of the secondary waves will terminate the negative phase. Furthermore, a long extension section 16 is typically used to allow a sufficient number of vents 50 such that the negative phase can be enhanced. A long extension section 16 also contributes to achieving an extended positive phase. Conversely, a short extension section 16 is typically used to achieve a short duration negative phase for some cases since the secondary waves terminate the negative phase. A short duration positive phase dictates a short driver section 12, which in turn allows the initial rarefaction wave to catch up to and severely diminish the lead shock if the extension section 16 is too long. Increasing the length of the driver section 12 to restore the shock pressure by delaying the rarefaction increases the positive impulse.

Both the long duration and short duration design goals, therefore, are difficult to obtain with a single shock tube 10. Thus, multiple shock tubes 10 may be used to satisfy particular design goals. Although multiple shock tubes 10 may be an acceptable solution since the tubes 10 can share support and operational systems, multiple shock tubes 10 increase the capital cost of a shock tube facility significantly and will likely require higher operational and maintenance expenditures relative to those associated with a single shock tube 10. A collection of extension sections 16, alternatively, can be provided, with the appropriate section 16 used for a given shock tube operation. However, the use of multiple extension sections 16 can increase the operational complexity and costs associated with the facility. An alternative to the use of multiple shock tubes 10 or extension sections 16 is the use of a single extension section 16 with an adjustable length.

Figure 15A:
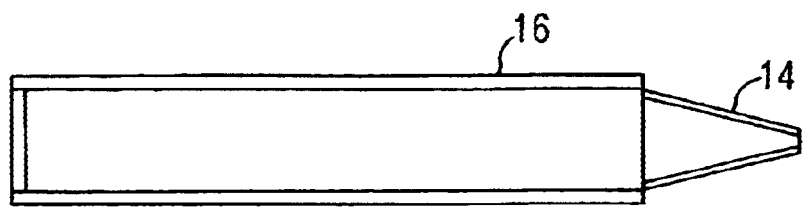
FIGS. 15a, 15b illustrate a cross-sectional, partial view of a shock tube with an adjustable extension section length, implemented herein in accord with one embodiment.
Figure 15B:
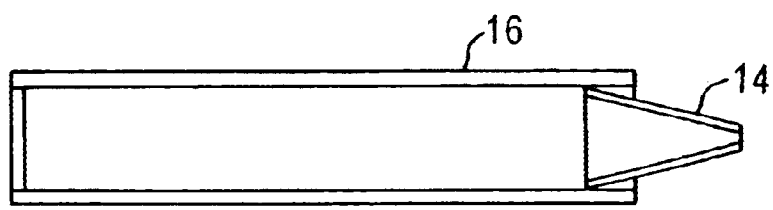

Although not limited in the manner described below, an extension section 16 with an adjustable length can be implemented using several approaches. As illustrated in FIGS. 15a, 15b, a first approach is to employ a "sliding" driver section and expansion section assembly 14. The driver section and expansion section assembly 14 can be moved into the extension section 16 to achieve a reduced extension section effective length, or be pulled back to increase its effective length.

This approach advantageously does not require any special arrangement to preserve the structural integrity of the extension section 16. For example, a rail or roller system (not shown) mounted inside the extension section 16 and extended back out towards the end of the driver section can be used to support movement of the driver section and expansion section assembly 14. This approach also does not interfere with operation of the vents between the target and expansion section 14.

A gap can be provided between the outer wall of the expansion section and inner wall of the extension section to allow for the expansion section motion. Such a gap acts as an additional vent at the junction between the expansion and extension sections. It is also possible to design a partial seal in order to limit the effective area associated with this vent path.

Figure 16A:
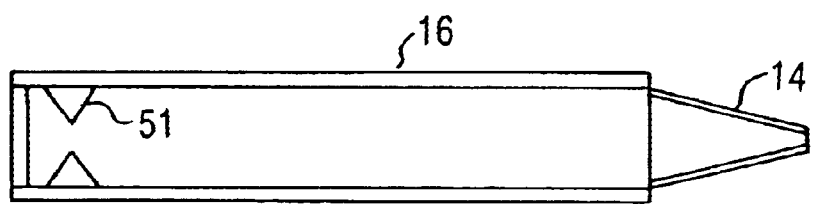
FIGS. 16a, 16b illustrate a cross-sectional, partial view of a shock tube with an adjustable extension section length in accord with another embodiment.
Figure 16B:
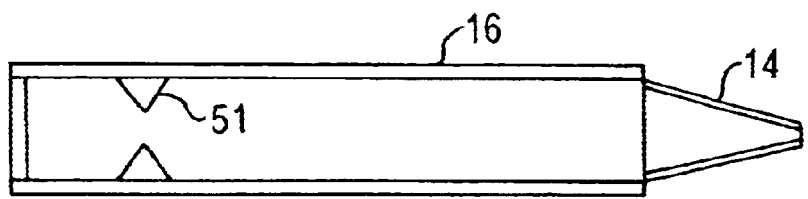

A second approach is similar to that outlined above, but the target would be moved within the extension section 16 to achieve the required effective extension length. As illustrated in FIGS. 16a, 16b, this approach would may require movable supports 51 within the extension section 16 to allow for mounting of the target. Furthermore, the target assembly can effectively seal off the extension section 16 to prevent wrap around of the load to the backside of the target.

Figure 17A:
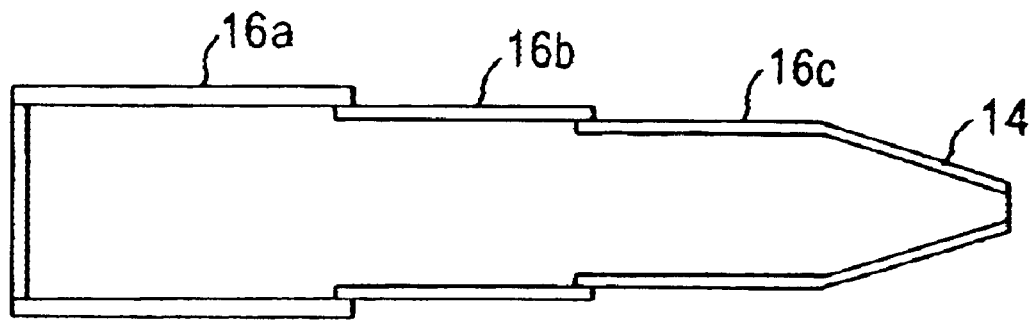
FIGS. 17a, 17b illustrate a cross-sectional, partial view of a shock tube with an adjustable extension section length in accord with still another embodiment.
Figure 17B:
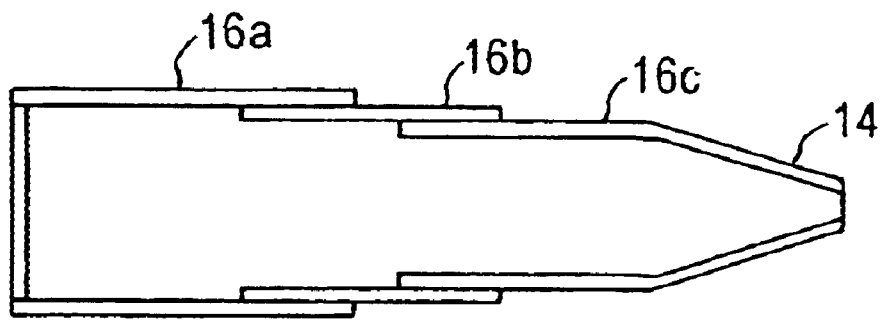

A third approach is to employ a telescoping extension section 16. As illustrated in FIGS. 17a, 17b, the driver section and expansion section 14 can be moved forward to collapse the extension section 16 to a reduced length, or be pulled back to stretch the extension section 16 to an increased length. Thus, the extension section 14 is formed of two or more segments 16a, 16b, 16c that are movable relative to one another. From an operational viewpoint, the vent assemblies in the portion of the section to be collapsed may have to be removed, and then put back into place once that portion is pulled back out again.

Referring back to FIG. 2, the shock tube 10 can also include shock absorbent material 80 positioned at the closed end 25 of the driver section 12. One function of the shock absorbent material is to reduce the intensity of the initial rarefaction wave reflection. This wave is created by the release of the initial shock (i.e., rupture of the diaphragm) and travels back down the driver section 12. The wave reflects off the closed end 25 of the driver section 12 and, depending on the shock tube configuration, can catch up to the main shock prior to the main shock reaching the target. This reduces the intensity of the main shock, and the pressure within and/or length of the driver section 12 is increased accordingly to achieve a specified target pressure.

An increase in driver pressure requires that the driver section 12 have a higher pressure capacities. Also, an increase in driver section length may be undesirable because it will impact target load histories.

The rarefaction wave can also produce undesirable target pressure perturbations. Another function of shock absorbent material 80 at the closed end 25 of the driver section 12 is to reduce the intensity of shock wave and secondary rarefaction reflections from this surface. The reflection of the main shock wave off the target and back down the shock tube 10 into the driver section 12 produces a second reflection off the closed end 25 of the driver section 12, which subsequently travels back down the tube 10 and impacts the target. This is undesirable since, depending on the tube configuration and operating conditions, it can prematurely terminate the negative phase and/or represent a significant secondary positive target load.

There are several sources that can produce shock waves that will enter the expansion section 14 heading towards the driver section 12. The reflection of the main shock off the target passes through the expansion section 14 prior to entering the driver section 12. A portion of the reflected shock will enter the driver section 12 and reflect off the back end 25 of the driver section 12, as discussed above. Some portion of the shock will reflect directly back towards the target. In addition, the strong pressure gradient established within the expansion section 14 will produce counter shocks traveling from the expansion section 14 towards the driver section 12. These shocks, along with the reflection of the main shock off the target entering the expansion section 14, will also interact and produce secondary waves. Some portion of these shock waves will reflect off the expansion section walls back towards the target as a secondary pressure or shock wave. The production of these secondary waves is undesirable since they can prematurely terminate the negative phase and/or represent a significant secondary positive target load.

As described herein, the shock absorbent materials act as "shock absorbers" more than "energy absorbers." Thus, while the peak pressure associated with a reflection off a surface to which the material is applied will decrease, the total impulse associated with the reflection is not expected to change significantly.

The only shock absorbent material tested in the expansion section 14, as illustrated in FIG. 7a, was sisal due to the retention requirements such that the shock and pressure waves passing through this section 15 do not displace the material. A retention device 81 is used to keep the shock absorbent material 80 in place. Although any retention device so capable is acceptable for use with the shock tube, in a current aspect, the retention device utilized to retain the sisal within the expansion section included $\frac{1}{16}$ inch thick flattened expanded metal panels ($\frac{1}{2}$ and $\frac{3}{4}$ inch openings), which were bolted to the expansion section.

Figure 18:
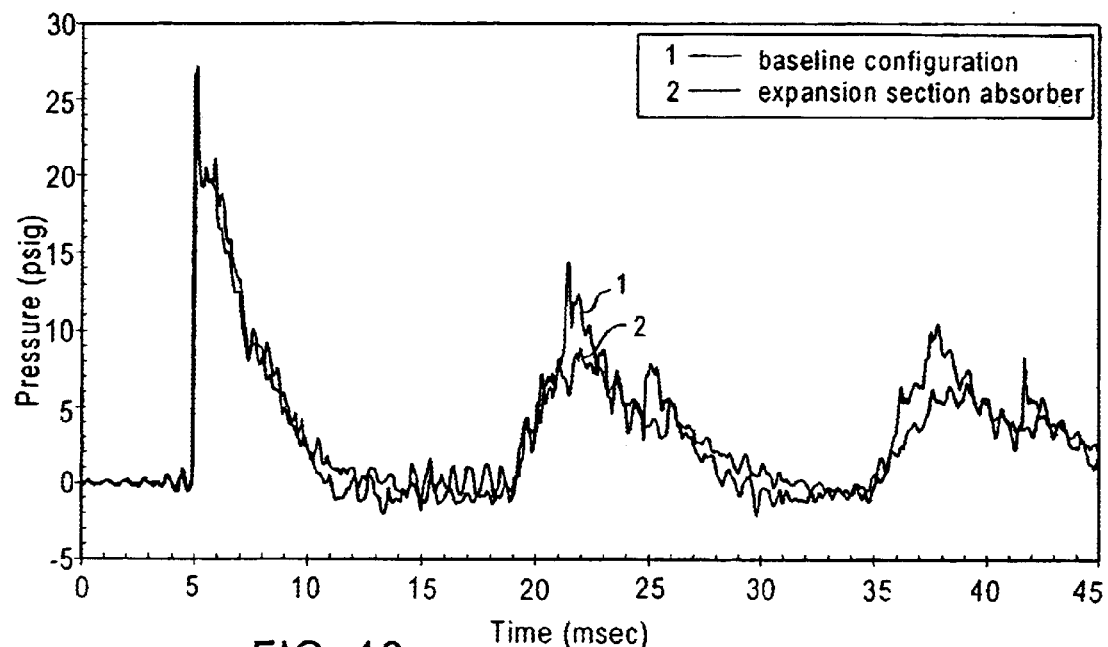
FIG. 18 is a graph of the effect of expansion section material for air at 400 psig.

FIG. 18 illustrates target pressure histories for the baseline configuration and with sisal in the expansion section for a driver section pressurized with nitrogen to 400 psig. There was no shock absorbent material in the driver section for this case. The presence of the sisal in the expansion section has very little effect on the pressure trace prior to the arrival of the secondary pressure and shock waves at the target. The peak pressure associated with the initial shock wave is only reduced by approximately 1%, and some reduction is expected since the edges of the shock wave will interact with the material in the expansion section and hence weaken the shock.

The positive phase is drawn out by a small amount, with the initiation of the negative phase slightly delayed. The total positive impulses of the two waves are within 2% of one another at 19 msec, which is the time at which the first secondary pressure wave arrives at the target. This wave is formed by the reflection of the main shock off the closed end of the driver section. The peak of the secondary pressure wave is decreased by approximately 40%, from just over 14 psig down to less than 9 psig. Thus, a significant potion of this pressure wave arises due to reflections off the expansion section.

The expansion section absorber is also effective at reducing the magnitude of the second of the pressure waves that load the target. The peak pressure of this shock, which arrives at 25 msec, is decreased by approximately 30%, from 8 psig down to slightly more than 5 psig. The impulse associated with these secondary waves does not appear to be significantly changed. For the case shown in FIG. 18, the impulses associated with the two waves from 19 to 35 msec, the time period over which the secondary waves load the target, are equal (46 psi-msec). The decrease in the magnitude of the reflections of these pressure waves, which arrive at 35 and 42 msec, respectively, is similar to those for the initial loadings by these waves.

Figure 19:
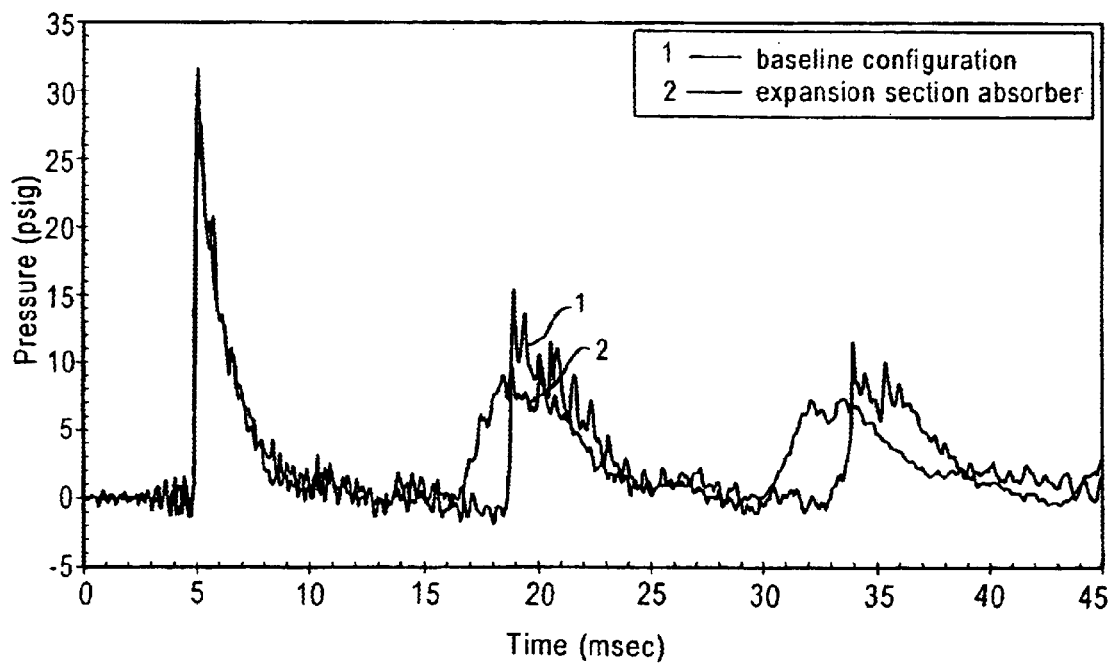
FIG. 19 is a graph of the effect of expansion section material for helium at 400 psig.

FIG. 19 illustrates target pressure histories for the baseline configuration and with sisal in the expansion section for a driver section pressurized with helium to 400 psig. This same configuration is discussed in connection with FIG. 18, but with helium rather than nitrogen as the driver gas. With regards to the secondary target loading, the baseline configuration pressure history for helium as the driver gas is different from that for nitrogen (FIG. 18) in that the secondary pressure waves essentially coalesce just before reaching the target, so that there are not two separate and distinct waves that load the target. Nevertheless, the secondary wave magnitude is approximately the same as that for the case of nitrogen as the driver gas.

The same type of reduction in secondary wave intensity due to the shock absorbent material in the expansion section is observed with helium as the driver gas as with nitrogen. However, with helium, the presence of the shock absorbent material results in a secondary wave loading which reaches the target a few milliseconds earlier. Although it is not clearly understood why this occurs with helium but not with air, it may be due simply to the higher shock velocity in the helium-air mixture present in the expansion section and front end of the extension section. In addition, the retention device utilized in the helium tests was more robust than that in the air test, such that it may offer more surface area for reflection.

Another difference between the pressure histories obtained with air versus helium driver gases with respect to the effectiveness of shock absorbent material in the expansion section is that the main shock peak pressure is reduced more with helium than with air. Thus, the application of shock absorbent material in the expansion section with a helium driver gas can be more effective at reducing the magnitude of the secondary pressure wave loading on the target. Furthermore, in the case of the helium driver gas, the presence of the shock absorbent material changes the secondary wave from a true shock to a pressure wave, so that the loading on the target would not be suddenly applied. This reduces the structural impact of the secondary wave loading for targets with relatively short natural periods.

Figure 20:
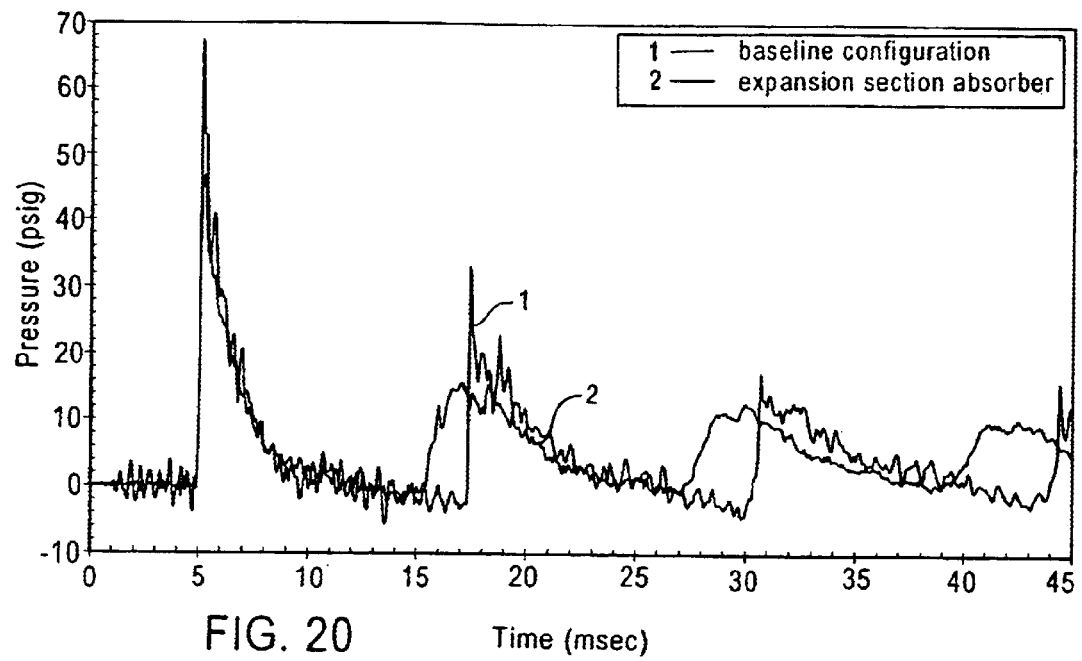
FIG. 20 is a graph of the effect of expansion section material for helium at 750 psig.
Figure 21:
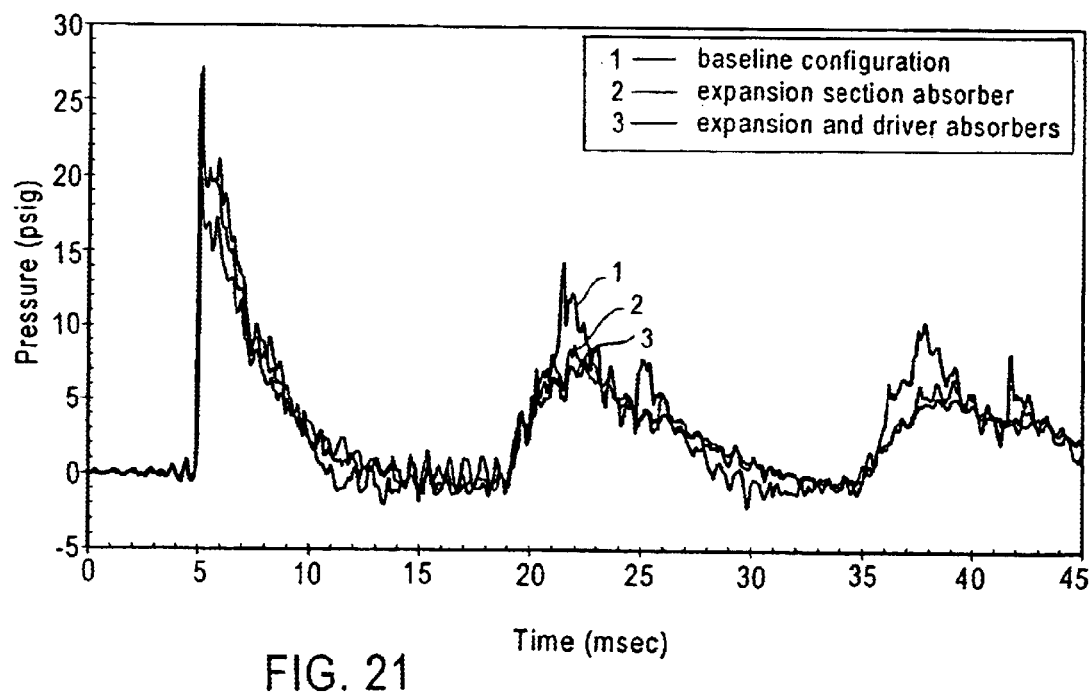
FIG. 21 is a graph of the effect of steel wool in the driver section for air at 400 psig.
Figure 22:
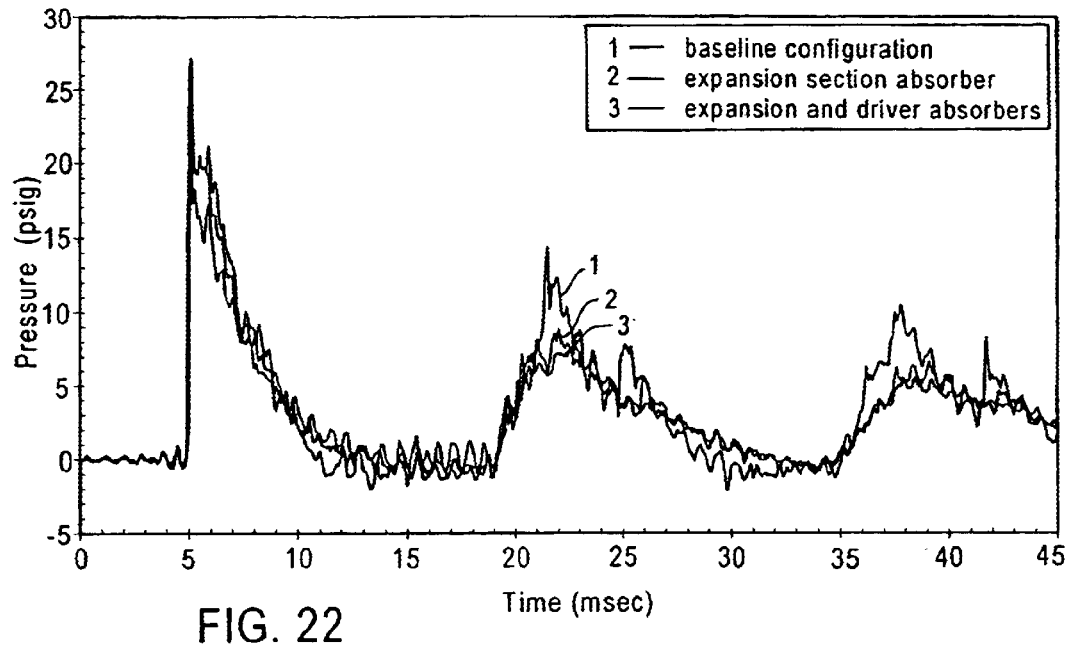
FIG. 22 is a graph of the effect of sisal in the driver section for air at 400 psig.
Figure 23:
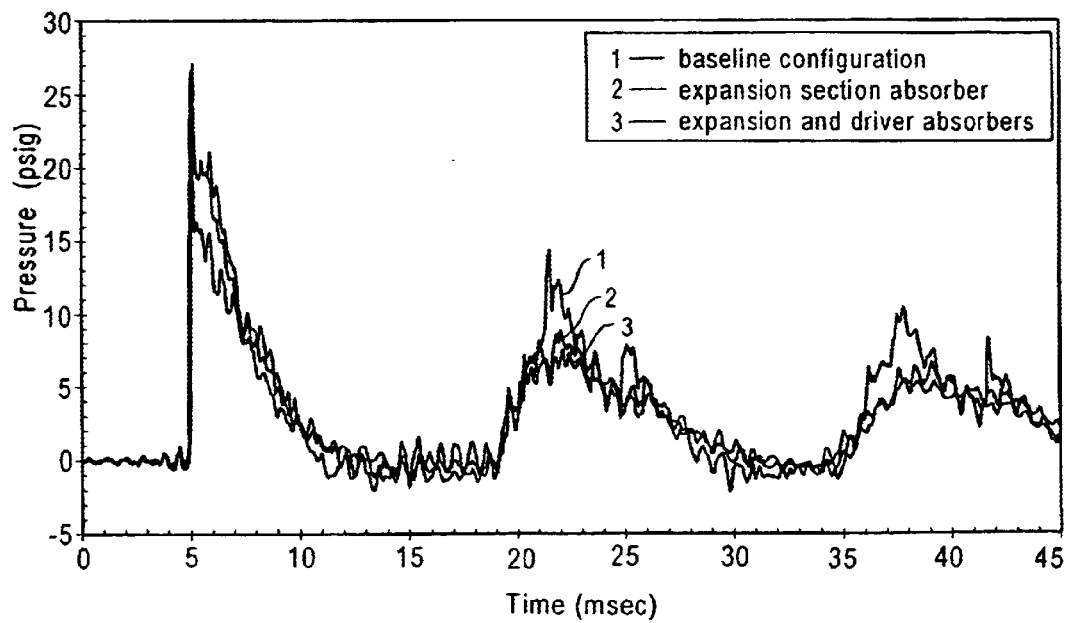
FIG. 23 is a graph of the effect of cut rubber in the driver section for air at 400 psig.
Figure 24:
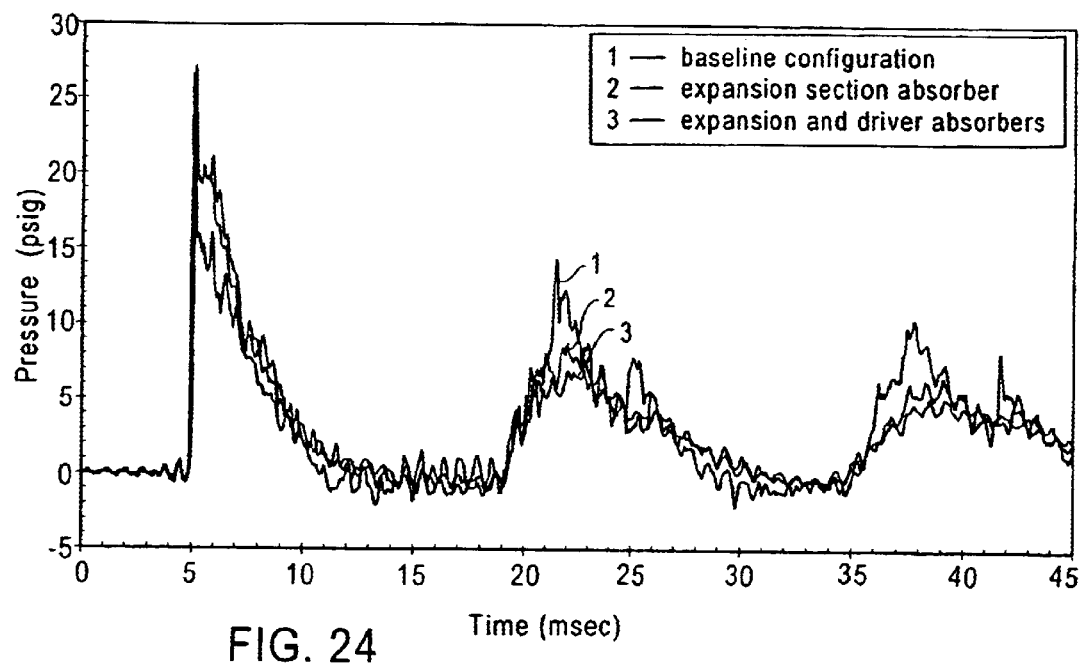
FIG. 24 is a graph of the effect of plastic beads in the driver section for air at 400 psig.
Figure 25:
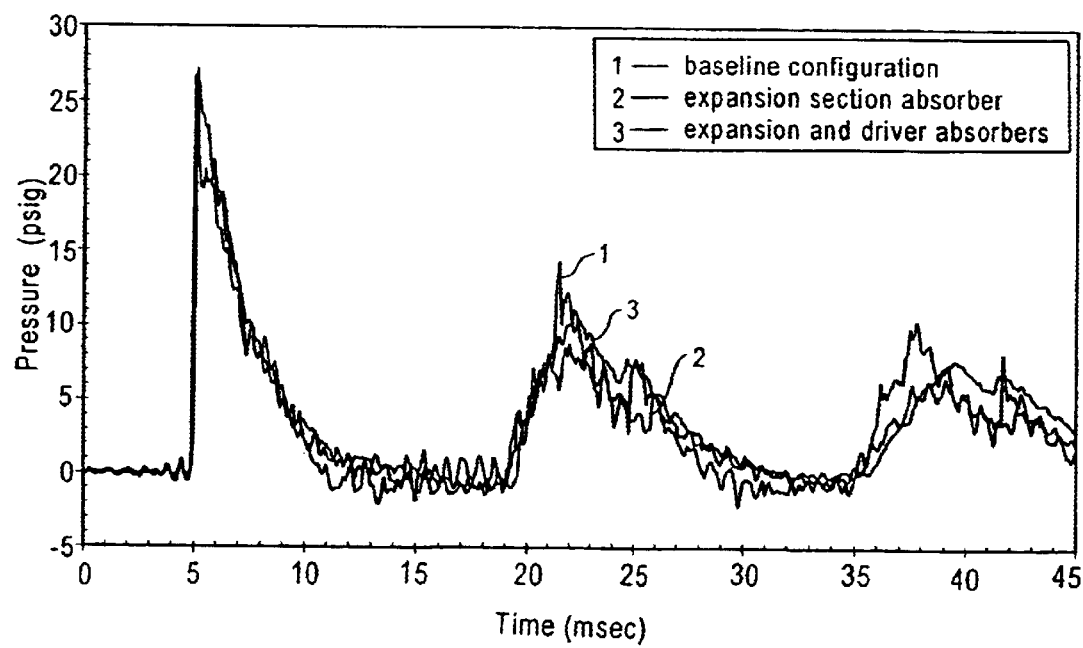
FIG. 25 is a graph of the effect of foam in the driver section for air at 400 psig.

FIG. 20 illustrates the target pressure histories for the baseline configuration and with sisal in the expansion section for a driver section pressurized with helium to 750 psig. This figure shows essentially the same features as that for a helium driver at 400 psig (FIG. 19). Hence, the impact of the expansion section shock absorbent material appears to be the same over a significant range of driver pressures.

Although smaller than the impact provided by vents, the impulse associated with the secondary waves is impacted by the presence of shock absorbent material in the expansion section. However, the relatively large impulse associated with these waves could be detrimental to the response of some targets. Thus, improvements to the target pressure history can be achieved by the application of shock absorbent material in the expansion section. It should be noted, however, that the application of shock absorbent material in the expansion section will likely require a robust retention mechanism.

A slight extension of the driver section from the diaphragm assembly into the expansion section can be used to shield the leading edge of the shock absorbent material from the main shock. Also, placing vents along the extension section can decrease the magnitude of secondary waves and their reflections, and hence lessen the significance of shock absorbent material in the expansion section. Although sisal was tested, other materials may function as good as, or better than, sisal. For example, open-celled reticulated polyester or metal foam are possible materials.

All of the tests performed to examine the impact of shock absorbent material in the driver section contained the expansion section sisal arrangement previously described. As discussed above, the reflection of the shock wave off the closed end of the driver section is significantly mitigated by the presence of shock absorbent material in the expansion section. Thus, the benefit gained by the application of shock absorbent material in the driver is masked to a certain degree, although the experimental results illustrate the benefit of such an arrangement.

The materials examined for application at the closed end of the driver section were steel wool, sisal, cut rubber, plastic beads, and open-cell reticulated polyester foam. FIGS. 21 through 25 illustrate target pressure histories with each of these materials, in the order listed above, for a driver section pressurized with air to 400 psig; the pressure histories without any material in the driver section are the same as those shown in FIG. 18. The test with the foam, shown as FIG. 25, utilized a stronger expansion section retention device than for the test shown in that figure for material in the expansion section only, so that the two pressure histories are not directly comparable. All other tests shown in this figure set utilized the weaker expansion section retention device and therefore are directly comparable.

The steel wool assembly utilized was comprised of two sections of 00 grade and one-half of a section of fine (#3), with the fine material placed at the rear of the assembly, which is nearest the closed end of the driver section. Rubber-coated sisal is essentially a loose fiber mat. The sisal employed during test was cut from nominal one inch and two inch thick layers. The cut rubber and plastic beads are typically very resistant to degradation and offer shock absorbent characteristics. A disc cut from the two inch thick sisal was used in front of both the cut rubber and plastic beads in order to prevent these materials from being displaced. The open-cell reticulated polyester foam can be readily tailored to a range of porosity distribution specifications, and hence provides a material that can be "tuned" to provide a desired response. Three sections of foam with different pore sizes were used to form the shock absorbent material assembly:

80, 45, and 20 pores per inch (PPI). Each foam section was 2 inches long, so that the assembly was 6 inches long. The foam with the largest pores (20 PPI) was used at the front of the assembly (i.e. facing the expansion section) and that with the smallest pores (80 PPI) was used at the back end.

An example of a device employed to retain the shock absorbent material in the driver section can consist of a pipe. One end of the pipe can be threaded onto a steel pipe nipple welded to a plate that slips between the driver section and driver end plate. This arrangement can fix the retention device at the back (i.e., closed) end of the driver section. A series of screens can then be placed at the other end of the pipe to retain the shock absorbent material.

As a general observation, the materials tested did not have as significant of an impact as that of the expansion section material relative to the baseline configuration. Thus, most of the gain relative to reducing the intensity of the secondary pressure waves is made by placing material in the expansion section, while the material in the driver makes a small contribution on a relative basis. However, the effect of the material in the driver section could appear more significant if there were no material in the expansion section.

All of the materials appear to be nearly equally effective at reducing the intensity of the secondary pressure wave. Also, except for the foam, all of the materials act to limit the jet pulse following the shock, so that the positive impulse in the first few milliseconds following the arrival of the shock at the target is limited. This occurs because the absorber material assembly acts as a baffle, slowing the release of gas from the driver. In the case of the foam, an examination of the pressure traces in the expansion section indicates that the diaphragms did not break cleanly, and thus the initial portion of this trace is somewhat suspect.

The steel wool, cut rubber, and plastic beads all resulted in a noticeable decrease in the peak shock pressure (approximately 4 to 7 psig), although this decrease only impacts the first fraction of a millisecond during the arrival of the shock at the target and thus would likely have a reduced impact on the positive impulse associated with the shock. Although the reason for this decrease is not completely understood at this time, it may be due to reflection of the rarefaction wave off the front of the absorber material. This decrease does not occur with the sisal or foam, both of which are more open (i.e., higher porosity) than the materials for which this effect is evident.

Figure 26:
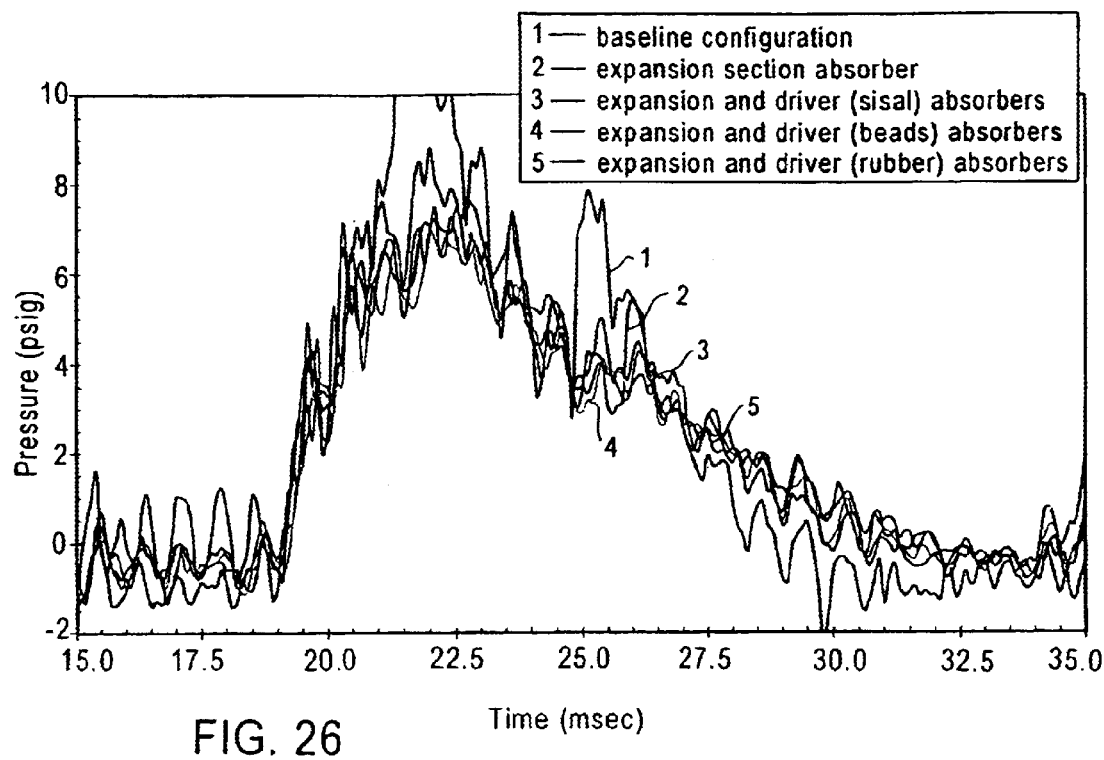
FIG. 26 is a graph of a comparison of driver absorber materials for air at 400 psig.

FIG. 26 illustrates a comparison between target pressure histories with sisal, cut rubber, and plastic beads used as the driver absorber materials. The scale utilized in this figure is reduced relative to those discussed above to highlight the impact of the absorbers on the secondary pressure wave. As can be seen directly in this figure, all three materials have a very similar impact on the pressure trace. Again, the differences between the materials may be more evident if no absorber material was present in the expansion section.

Figure 27:
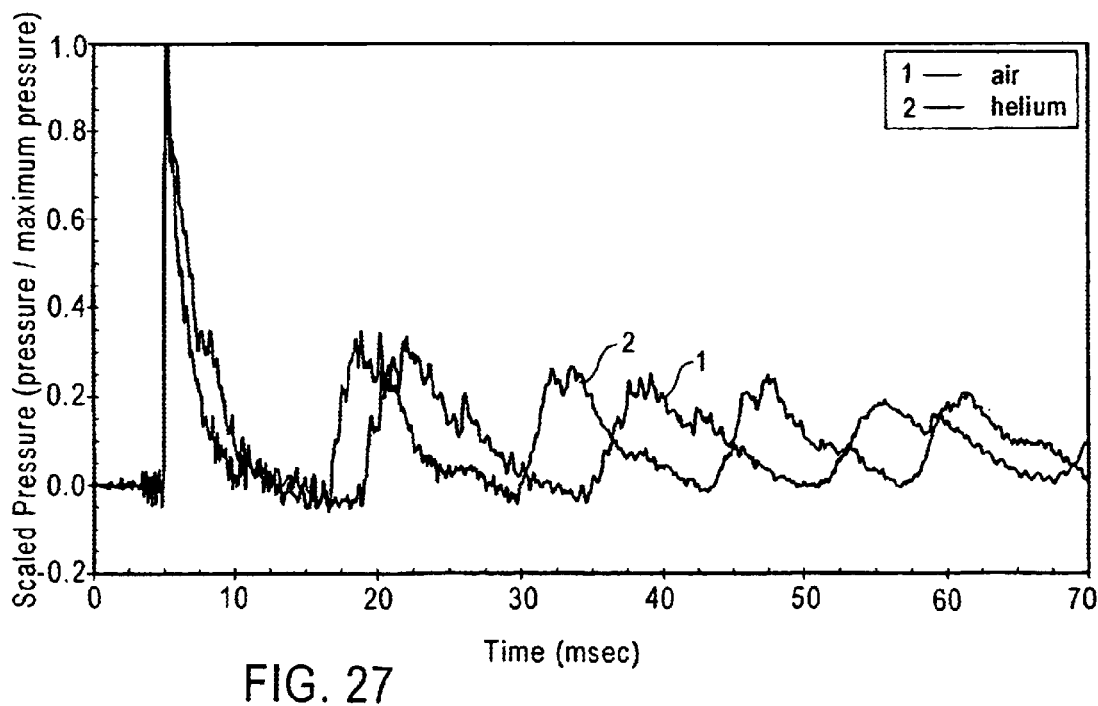
FIG. 27 is a graph of the effect of sisal in the driver section for air at 750 psig.

The effect of sisal in the expansion and driver sections for a driver section pressurized with air to 750 psig is illustrated in FIG. 27. The effect is similar to that for air at 400 psig. The reduction in the positive impulse associated with the initial portion of the loading is not as significant as at 400 psig.

Figure 28:
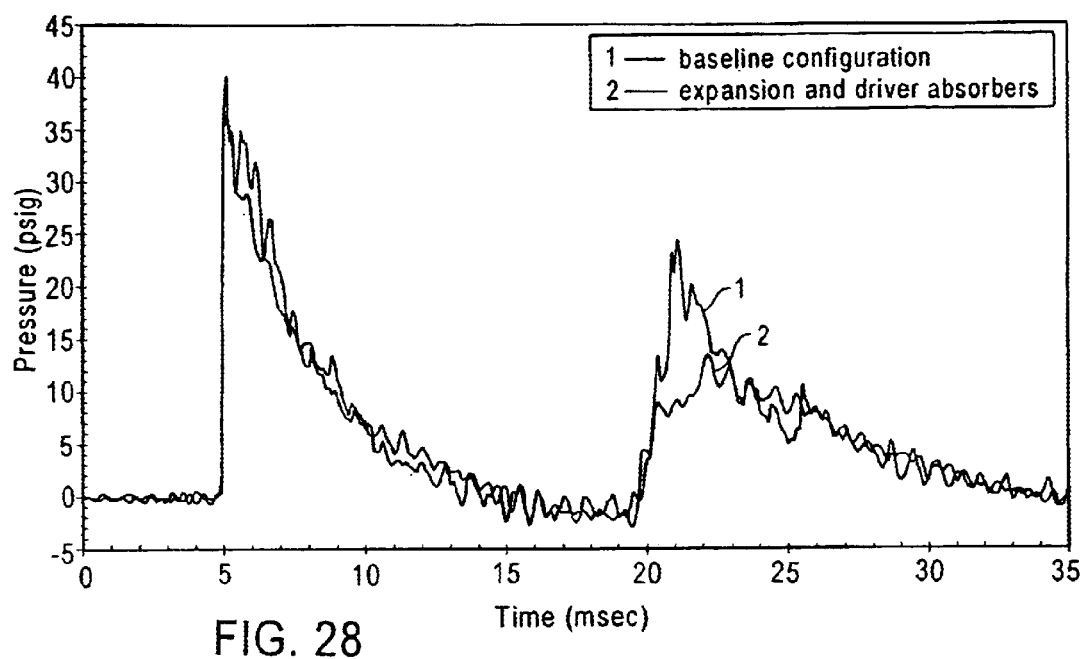
FIG. 28 is a graph of a comparison of sisal in the driver section for air and helium at 400 psig.

FIG. 28 illustrates a comparison between the pressure histories for air and helium driver gases at 400 psig with sisal in the expansion and driver sections. The y-axis of this plot is expressed in terms of relative pressure (pressure divided by maximum pressure) since the peak pressure for helium is greater than that for air at the same driver pressure. The effect of the combined expansion and driver absorbent material assemblies is similar for both driver gases.

Figure 29:
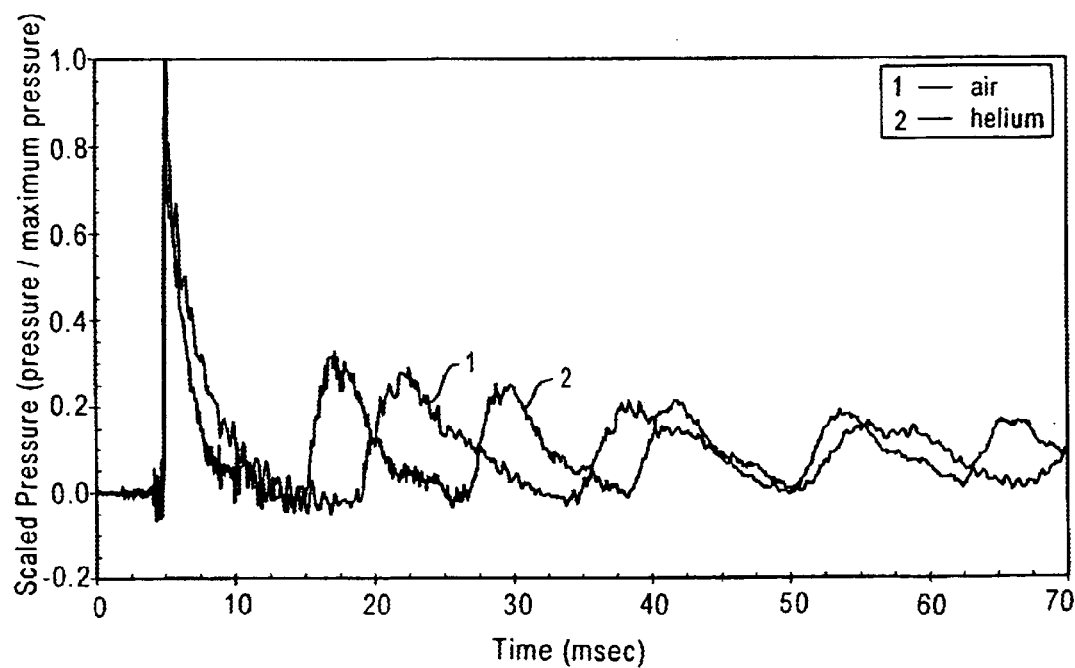
FIG. 29 is a graph of a comparison of sisal in the driver section for air and helium at 750 psig.

FIG. 29 illustrates the same information for a driver pressure of 750 psig. Again, the effect is similar for both driver gases. These pressure histories do illustrate that the positive impulse associated with helium is less than that for air and the negative phase obtained with helium is reduced slightly relative to that for air at the same driver length.

The above-described invention provides significant benefits over the prior art. For example, the amplitude of secondary shock and pressure waves originating in the expansion and driver sections can be decreased significantly by the application of shock absorbent material. Also, use of an active vent decreases the positive phase impulse and duration and limits the intensity of secondary pressure and shock waves. By employing active vents along the length of the extension section, an increase in both the duration and amplitude of the negative phase can be obtained. The negative phase parameters can be controlled by the total amount of vent area made available and the mixture of active and open-only vents employed. The negative phase parameters can be further controlled by the distribution of active and open-only vents along the length of the extension section. Adjustable driver and extension section lengths allow a single shock tube to produce a wide range of positive and negative phase target pressure loadings.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only an exemplary aspect of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A shock tube, comprising:
    a driver section;
    an extension section connected to the driver section; and
    shock absorbent material,
    wherein the driver section and extension section define a cavity and the shock absorbent material is disposed within the cavity.

2. The shock tube according to claim 1, wherein the extension section includes sidewalls, and the shock absorbent material is disposed on the sidewalls.

3. The shock tube according to claim 1, wherein the driver section includes a end wall oppositely disposed from the extension section, and the shock absorbent material is disposed proximate to the end wall.

4. The shock tube according to claim 1, wherein the extension section includes an expansion section connecting the extension section to the driver section.

5. The shock tube according to claim 4, wherein the expansion section includes sidewalls, and the shock absorbent material is disposed on the sidewalls.

6. The shock tube according to claim 1, further comprising a retention device for securing the shock absorbent material within the cavity.

7. A shock tube, comprising:
   a driver section defining a chamber;
   an extension section connected to the driver section at one end of the extension section, and the extension section being open at an opposite end of the extension section; and
   at least one active vent connected to a cavity defined by the extension section, wherein in one mode, a fluid connection exists between the cavity and the chamber, and in another mode, the cavity is fluidly separated from the chamber.

8. A shock tube, comprising:
   a driver section;
   an extension section connected to the driver section; and
   at least one active vent disposed over a respective hole in the extension section connected to a cavity defined by the extension section, wherein the at least one active vent is positionable in at least two positions and includes a vent cover and resilient members, and
   in a first position, the vent cover covers the hole in the extension section to prevent fluid from escaping the cavity from the hole, and
   in a second position, the hole in the extension section is uncovered.

9. A shock tube, comprising:
   a driver section;
   an extension section connected to the driver section; and
   at least one active vent disposed over a respective hole in the extension section connected to a cavity defined by the extension section, wherein the at least one active vent is positionable in at least two positions and includes a piston having a vent cover, and
   in a first position, the vent cover covers the hole in the extension section to prevent fluid from escaping the cavity from the hole, and
   in a second position, the hole in the extension section is uncovered.

10. The shock tube according to claim 9, wherein the piston includes an upper piston head connected to the vent.

11. The shock tube according to claim 10, wherein the at least one active vent includes a dashpot connected to the upper piston head.

12. A shock tube, comprising:
    a driver section;
    an extension section connected to the driver section; and
    at least one active vent disposed over a respective hole in the extension section connected to a cavity defined by the extension section, wherein the extension section includes an expansion section connecting the extension section to the driver section.

13. The shock tube according to claim 12, wherein the expansion section includes the at least one active vent.

14. The shock tube according to claim 7, wherein the shock tube includes two or more active vents that are separate from one another.

15. The shock tube according to claim 7, wherein the shock tube includes two or more active vents connected together with a common manifold.

16. A shock tube, comprising:
    a driver section;
    an extension section connected to the driver section; and
    wherein the extension section is slidably adjustable between one of at least two positions relative to the driver section, and a length of the extension section in a first position is longer than a length of the extension section in a second position.

17. The shock tube according to claim 16, wherein the extension section includes an expansion section connecting the extension section to the driver section and the expansion section is movable within extension section.

18. The shock tube according to claim 16, further comprising a support for holding a target, and the support is adjustably positionable within the extension section.

19. The shock tube according to claim 16, wherein the extension section includes two or more segments that are movable relative to another to change a length of the extension section.

20. The shock tube according to claim 16, wherein the extension section includes an expansion section connecting the extension section to the driver section.

* * * * *